United States Patent [19]

Ku

[11] Patent Number: 4,981,848
[45] Date of Patent: Jan. 1, 1991

[54] ALPHA-ADRENERGIC RECEPTOR ANTAGONISTS

[75] Inventor: Thomas W. Ku, Dresher, Pa.

[73] Assignee: SmithKline Beecham Corporation, Philadelphia, Pa.

[21] Appl. No.: 314,722

[22] Filed: Feb. 23, 1989

[51] Int. Cl.$^5$ .................... A61K 31/55; C07D 223/00
[52] U.S. Cl. .................................... 514/215; 540/581
[58] Field of Search ........................ 540/581; 514/215

[56] References Cited

U.S. PATENT DOCUMENTS

| | | | |
|---|---|---|---|
| 3,833,591 | 9/1974 | McManus | 540/581 |
| 3,904,645 | 9/1975 | McManus | 540/581 |
| 3,906,000 | 9/1975 | McManus | 540/581 |
| 4,469,634 | 9/1984 | DeMarinis | 540/581 |
| 4,567,177 | 1/1986 | Piggi et al. | 540/581 |
| 4,769,368 | 9/1958 | Kaiser et al. | 514/217 |

FOREIGN PATENT DOCUMENTS

| | | | |
|---|---|---|---|
| 0030176 | 2/1981 | Japan . | |
| 87/00522 | 1/1987 | PCT Int'l Appl. | 514/215 |

OTHER PUBLICATIONS

Sanger, Pharmacology, 1988, pp. 413–417.
Broadstone et al., Diabetes, 39, 1987, pp. 932–937.
Greenway et al., Clinical Therapeutics 9 (6), 1987, 663–9.
Galitzky et al., Clinical Investigation, 1988, 18, 587–94.
Cubeddu, American Heart J., 1988, pp. 133–163.
Hieblo et al., Eup. J of Pharmacology, 107(1985), 111–7.
Caine, Virology, Dec. 1988, XXXII(6), 16–20.
Tsukamoto et al., Biological Psychiatry, 19(9), 1984, 1283–91.

Primary Examiner—Mukund J. Shah
Assistant Examiner—E. C. Ward
Attorney, Agent, or Firm—Mary E. McCarthy; Stuart R. Suter; Edward T. Lentz

[57] ABSTRACT

Alpha-adrenoceptor antagonists having the formula:

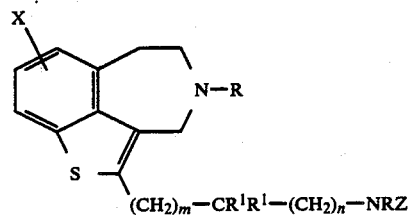

which are useful to produce α-adrenoceptor antagonism, pharmaceutical compositions including these antagonists, and methods of using these antagonists to produce α-adrenoceptor antagonism in mammals.

18 Claims, No Drawings

ALPHA-ADRENERGIC RECEPTOR ANTAGONISTS

FIELD OF THE INVENTION

This invention relates to novel substituted 2-aminoalkyl-3,4,5,6-tetrahydrothieno[4,3,2-ef][3]benzazepine compounds that are α-adrenergic receptor antagonists.

BACKGROUND OF THE INVENTION

The autonomic nervous system is separated into the cholinergic and adrenergic nervous systems. Norepinephrine, the neurotransmitter of the adrenergic nervous system, exerts its activity by interaction with receptors (adrenoceptors) on the effector organs or on the nerve endings. The adrenoceptors are of two primary types: α and β. Based upon selectivity of the receptors for a series of agonists and antagonists, the α adrenoceptors have been subdivided into $\alpha_1$ and $\alpha_2$ subtypes.

A large amount of experimental evidence now supports the view that the $\alpha_2$ subtype is a heterogeneous adrenoceptor class. (For a general review see Timmermans and Van Zwieten, J. Med. Chem., 25, 1389 (1982)). Experiments using 6-chloro-9-(3-methyl-2-butenyloxy)-3-methyl-2,3,4,5-tetrahydro-1H-3-benzazepine (SK&F 104078) demonstrated that the classical adrenoceptors are heterogeneous and can be divided into SK&F 104078-insensitive and SK&F 104078 - sensitive $\alpha_2$ adrenoceptors. The latter variously are referred to as post-junctional $\alpha_2$ adrenoceptors or, preferably, $\alpha_3$ adrenoceptors, U.S. Pat. No. 4,683,229, July 28, 1987.

As one of the primary regulators of peripheral vascular tone, α adrenoceptors long have been the targets of efforts to develop agents effective in changing vascular tone for use in treating diseases, such as hypertension, in which alterations in vascular resistance produce therapeutic benefits. Antihypertensive compounds presently in clinical use that function via interaction with α adrenoceptors include methyldopa, clonidine, and prazosin. Efforts to modulate sympathetic tone through interactions with α adrenoceptors have resulted in several compounds that interact somewhat selectively with $\alpha_1$ or $\alpha_2$ adrenoreceptors. Selective agonists include phenylephrine and methoxamine which preferentially activate $\alpha_1$ receptors; and clonidine, α-methylnorepinephrine, and tramazoline which preferentially activate $\alpha_2$ adrenoceptors. Examples of selective α-adrenoceptor antagonists include prazosin which has high selectivity for $\alpha_1$ adrenoceptors; and the $\alpha_2$-selective blockers yohimbine and rauwolscine.

U.S. Pat. No. 4,469,634, describes allyloxy- and allylthio- 2,3,4,5-tetrahydro-1H-3-benzazepines useful as intermediates for preparing $\alpha_2$ adrenoceptor affinity resins and as antihypertensive agents.

U.S. Pat. Nos. 3,833,591, 3,904,645, and 3,906,000 disclose substituted compounds of the following base structure:

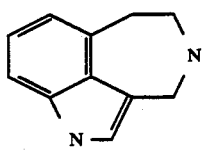

These compounds are disclosed as having utility as hypoglycemic agents.

PCT Application No. WO 87/00522 describes a series of 4-aminotetrahydrobenz[c,d]indoles and tetrahydroazepino[3,4,5-c,d]indoles having the general formula:

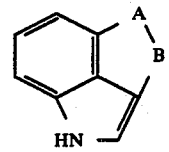

in which A-B is —CH$_2$—CH(NRR)—CH$_2$ or —CH$_2$—CH$_2$—NR—CH$_2$. These compounds are disclosed as having utility as dopamine agonists in the treatment of hypertension.

SUMMARY OF THE INVENTION

The present invention resides in the discovery that various substituted 2-aminoalkyl-3,4,5,6-tetrahydrothieno[4,3,2-ef][3]benzazepine compounds are α-adrenoceptor antagonists. Presently preferred compounds of the invention include:

N-[(7-chloro-3,4,5,6-tetrahydro-4-methylthieno[4,3,2-ef][3]benzazepin-2-yl)methyl]-2-methylpropanesulfonamide;

7-chloro-3,4,5,6-tetrahydro-4-methylthieno[4,3,2-ef][3]benzazepine-2-methanamine;

N-[(7-chloro-3,4,5,6-tetrahydro-4-methylthieno[4,3,2-ef][3]benzazepin-2-yl)methyl]-2-phenylethenesulfonamide;

N-[(7-chloro-3,4,5,6-tetrahydro-4-methylthieno[4,3,2-ef][3]benzazepin-2-yl)methyl]-2-benzeneethanesulfonamide; and N-[(7-chloro-3,4,5,6-tetrahydro-4-methylthieno[4,3,2-ef][3]benzazepin-2-yl)methyl]-2-benzenesulfonamide.

In a further aspect of the invention there are provided methods of antagonizing α adrenoceptors in mammals, including humans, that comprise administering internally to a subject an effective amount of a substituted 2-aminoalkyl-3,4,5,6-tetrahydrothieno[4,3,2-ef][3]benzazepine compound.

Included in the present invention are pharmaceutical compositions that include compounds useful in the method of the invention and a suitable pharmaceutical carrier. Preferably these compositions are used to produce α-adrenoceptor antagonism and contain an effective amount of compounds useful in the methods of the invention.

DETAILED DESCRIPTION OF THE INVENTION

The presently invented compounds that are α-adrenoceptor antagonists or are useful in preparing α-adrenoceptor antagonists are represented by the following Formula (I):

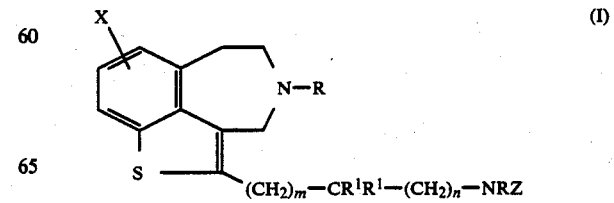

in which:

X is H, F, Cl, Br, I, CF$_3$, C$_{1-6}$alkyl, COR$^2$, CO$_2$R$^2$, CONR$^3$R$^3$, CN, NO$_2$, NR$^4$R$^1$, OR$^4$, SC$_{1-4}$alkyl, S(CH$_2$)$_{0-6}$aryl, SCF$_3$, or any accessible combination thereof of up to three substituents;

each R independently is H, C$_{1-6}$alkyl, or C$_{3-5}$alkenyl, except where the double bond is in the 1-position;

each R$^1$ independently is H or C$_{1-6}$alkyl;

Z is R, COR$^5$, CONR$^3$R$^6$, CO$_2$R$^8$, or SO$_2$R$^7$;

m and n are each 0 to 2, but m+n is not greater than 2;

each R$^2$ independently is C$_{1-6}$alkyl or (CH$_2$)$_{0-6}$aryl;

each R$^3$ independently is H, C$_{1-6}$alkyl, or (CH$_2$)$_{0-6}$aryl;

each R$^4$ independently is H, C$_{1-6}$alkyl, COR$^2$, or SO$_2$R$^2$;

R$^5$ is H, C$_{1-6}$alkyl, (CH$_2$)$_{0-6}$aryl, CH=CHaryl, C$_{3-5}$alkenyl, (CH$_2$)$_{1-3}$Oaryl, (CH$_2$)$_{1-3}$Saryl, or (CH$_2$)$_{1-3}$OR$^1$;

R$^6$ is H, C$_{1-6}$alkyl, (CH$_2$)$_{0-6}$aryl, (CH$_2$)$_{2-3}$Oaryl, (CH$_2$)$_{2-3}$Saryl, or (CH$_2$)$_{2-3}$OR$^1$;

R$^7$ is C$_{1-6}$alkyl, (CH$_2$)$_{0-6}$aryl, CH=CHaryl, C$_{3-5}$alkenyl, (CH$_2$)$_{1-3}$Oaryl, (CH$_2$)$_{1-3}$Saryl, or (CH$_2$)$_{1-3}$OR$^1$; and R$^8$ is C$_{1-6}$alkyl, (CH$_3$)$_{0-6}$aryl, (CH$_2$)$_{2-3}$Oaryl, (CH$_2$)$_{2-3}$Saryl, or (CH$_2$)$_{2-3}$OR$^1$; or a pharmaceutically acceptable salt thereof.

As used herein C$_{1-6}$alkyl means straight or branched alkyl of one to six carbon atoms, C$_{3-5}$alkenyl means a straight or branched chain alkenyl having from 3 to 5 carbon atoms, aryl means a phenyl group substituted by up to three X groups, and "accessible combination thereof" means any combination of up to three substituents on the phenyl moiety that is available by chemical synthesis and is stable. Formula (Ia) includes presently preferred Formula (I) compounds:

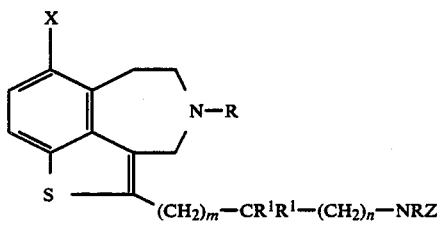

(Ia)

in which:

X is H, F, Cl, Br, I, CF$_3$, C$_{1-6}$alkyl, COR$^2$, CO$_2$R$^2$, CONR$^3$R$^3$, CN, NO$_2$, NR$^4$R$^1$, OR$^4$, SC$_{1-4}$alkyl, S(CH$_2$)$_{0-6}$aryl, SCF$_3$, or any accessible combination thereof of up to three substituents;

each R independently is H, C$_{1-6}$alkyl, or C$_{3-5}$alkenyl, except where the double bond is in the 1-position;

each R$^1$ independently is H or C$_{1-6}$alkyl;

Z is R, COR$^5$, CONR$^3$R$^6$, CO$_2$R$^8$, or SO$_2$R$^7$;

m and n are each 0 to 2, but m+n is not greater than 2;

each R$^2$ independently is C$_{1-6}$alkyl or (CH$_2$)$_{0-6}$aryl;

each R$^3$ independently is H, C$_{1-6}$alkyl or (CH$_2$)$_{0-6}$aryl;

each R$^4$ independently is H, C$_{1-6}$alkyl, COR$^2$, or SO$_2$R$^2$;

R$^5$ is H, C$_{1-6}$alkyl, (CH$_2$)$_{0-6}$aryl, CH=CHaryl, C$_{3-5}$alkenyl, (CH$_2$)$_{1-3}$Oaryl, (CH$_2$)$_{1-3}$Saryl, or (CH$_2$)$_{1-3}$OR$^1$;

R$^6$ is H, C$_{1-6}$alkyl, (CH$_2$)$_{0-6}$aryl, (CH$_2$)$_{2-3}$Oaryl, (CH$_2$)$_{2-3}$Saryl, or (CH$_2$)$_{2-3}$OR$^1$;

R$^7$ is C$_{1-6}$alkyl, (CH$_2$)$_{0-6}$aryl, CH=CHaryl, C$_{3-5}$alkenyl, (CH$_2$)$_{1-3}$Oaryl, (CH$_2$)$_{1-3}$Saryl, or (CH$_2$)$_{1-3}$OR$^1$; and R$^8$ is C$_{1-6}$alkyl, (CH$_2$)$_{0-6}$aryl, (CH$_2$)$_{2-3}$Oaryl, (CH$_2$)$_{2-3}$Saryl, or (CH$_2$)$_{2-3}$OR$^1$; or a pharmaceutically acceptable salt thereof.

Compounds of Formula (I) are prepared by the synthetic pathways shown in Schemes I through III. In Schemes I through III, X is as defined in Formula (I).

SCHEME I

Method A

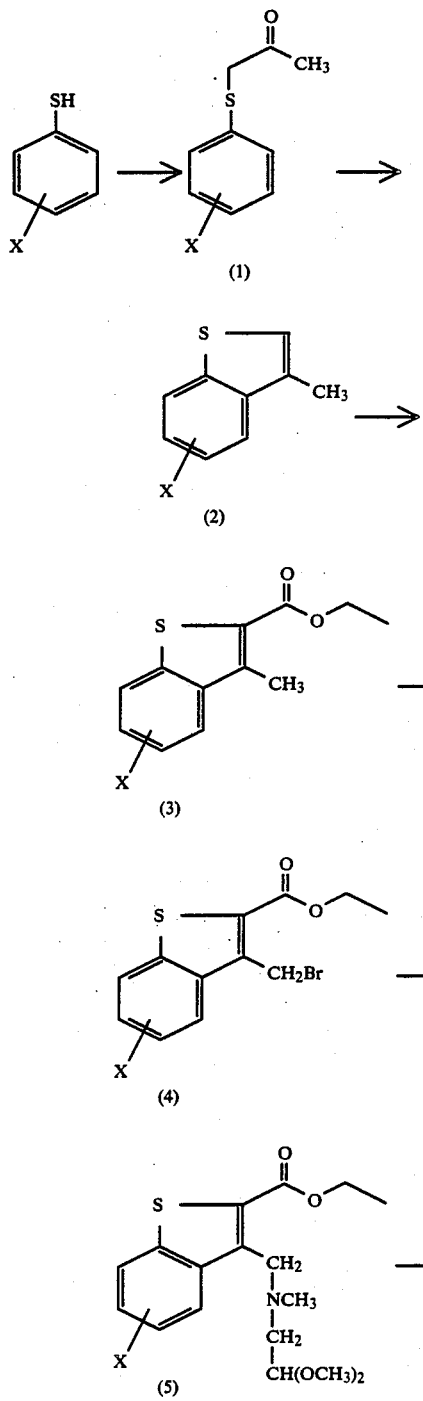

SCHEME I (continued)

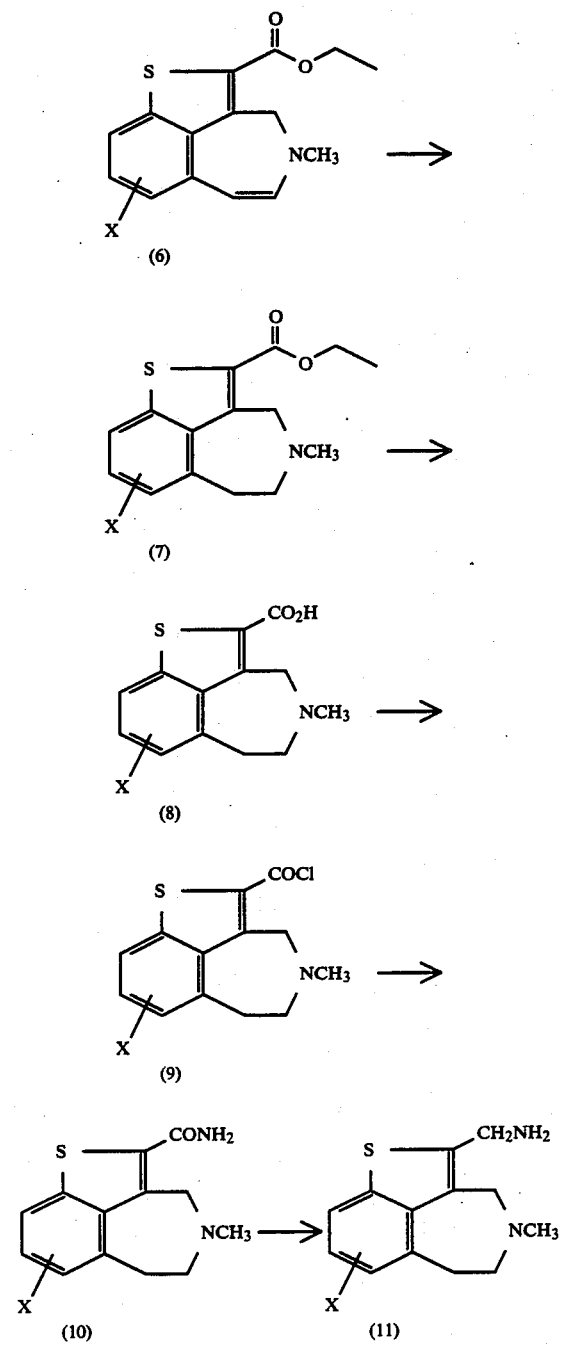

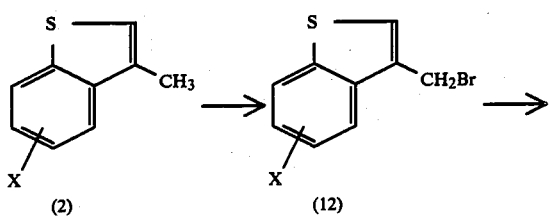

Method B

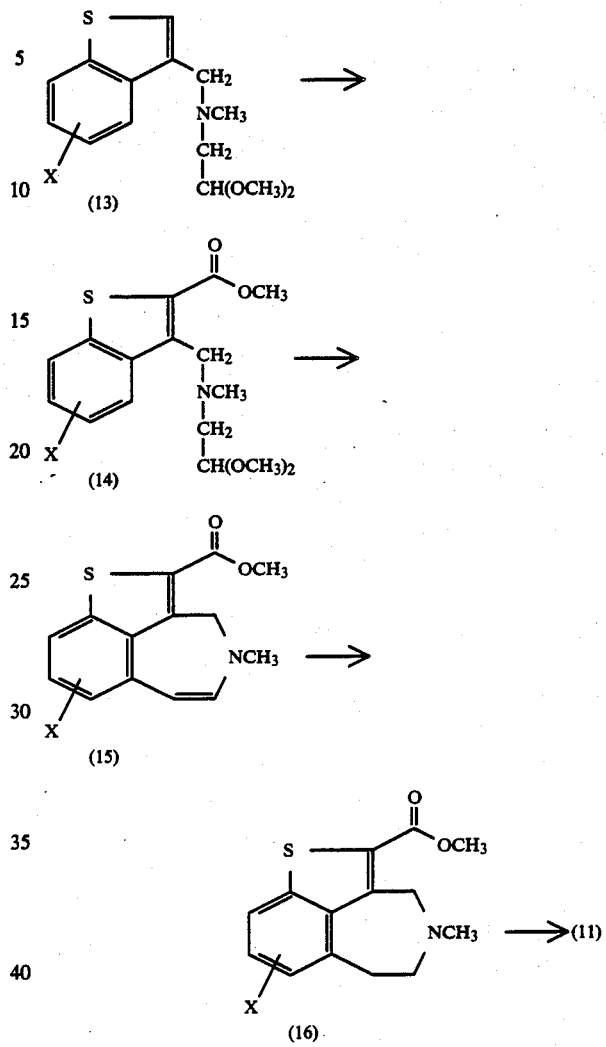

Scheme I, Method A, shows the synthesis of Formula (I) compounds in which the 2-position substituent is $CH_2NH_2$. These compounds are α-adrenoceptor antagonists and they are also useful as intermediates in the synthesis of other Formula (I) compounds. In Scheme I, X is as defined in Formula (I) and the R group attached to the nitrogen of the azepine ring is represented by a methyl group.

According to Scheme I, thiophenol or a substituted thiophenol is treated with a base, such as sodium hydroxide, in a suitable solvent, such as water. The resulting sodium thiophenolates are heated at 0° C. to 75° C., preferably about 25° C., with a haloacetone, preferably chloroacetone to yield (phenylthio)propanones (1). Substituted benzo[b]thiophene formula (2) compounds are prepared by treating formula (1) compounds with a strong acid, preferably polyphosphoric acid (PPA), at from 0° C. to 175° C., preferably 25° C. to 130° C.

Formula (2) compounds are treated with a strong base, preferably butyllithium, in an inert solvent, preferably ethyl ether, at a suitable temperature, preferably 0° C., and then with an alkyl chloroformate, preferably ethyl chloroformate, at a suitable temperature, preferably 0° C., to produce formula (3) compounds.

Formula (3) compounds are treated with a halogenating agent, preferably N-bromosuccinimide (NBS), and an initiator, preferably dibenzoylperoxide, in an inert organic solvent, preferably carbon tetrachloride (CCl₄), preferably at reflux, to produce formula (4) compounds. Formula (5) compounds are prepared by dissolving formula (4) compounds in an organic solvent such as acetone and adding a suitable base, preferably potassium carbonate (K₂CO₃), and an N-(C₁₋₆alkyl)aminoacetaldehyde di(C₁₋₄alkyl) acetal, preferably methylaminoacetaldehyde dimethyl acetal.

Formula (5) compounds are treated with acid, preferably trifluoromethanesulfonic acid, to yield enamine compounds of formula (6). Formula (6) compounds are treated with a reducing agent, preferably diborane, in an inert organic solvent such as tetrahydrofuran at a suitable temperature, such as at reflux, or reduced catalytically with a suitable catalyst, preferably platinum oxide, in a suitable solvent, preferably ethanol, to give benzazepine compounds of formula (7).

Thereafter, formula (7) compounds are hydrolyzed to formula (8) compounds with a strong acid, preferably concentrated hydrochloric acid, in a suitable solvent, preferably acetic acid. These formula (8) compounds are converted to acid chlorides by treatment with a suitable reagent, such as thionyl chloride, to yield formula (9) compounds. Formula (9) compounds are reacted with an amine, such as concentrated ammonium hydroxide solution saturated with ammonia gas, to give formula (10) amide compounds. Formula (10) compounds are treated with a reducing agent, preferably diborane, in an inert organic solvent, such as tetrahydrofuran, to give benzazepine-2-methylamine compounds of formula (11).

Scheme I, Method B, shows an alternate synthesis of Formula (I) compounds in which the 2-position substituent is CH₂NH₂. According to this synthetic route, the intermediate prepared is a Formula (I) related compound in which the 2-position substituent is CO₂CH₃.

Formula (2) compounds are treated with a halogenating agent, preferably N-bromosuccinimide (NBS), and an initiator, preferably dibenzoylperoxide, in an inert organic solvent, preferably carbon tetrachloride (CCl₄), preferably at reflux, to produce formula (12) compounds.

Formula (13) compounds are prepared by dissolving formula (12) compounds in an organic solvent such as acetone and adding a suitable base, preferably potassium carbonate (K₂CO₃), and an N-(C₁₋₆ alkyl)aminoacetaldehyde di(C₁₋₄ alkyl) acetal, preferably methylaminoacetaldehyde dimethyl acetal.

Formula (13) compounds are treated with a strong base, preferably butyllithium, in an inert solvent, preferably ethyl ether, at a suitable temperature, preferably −30° C., and then with carbon dioxide to produce carboxylic acids which are treated with an esterifying agent, such as diazomethane, in an inert solvent, such as ethyl ether, to give formula (14) compounds.

Formula (14) compounds are converted to formula (15), formula (16), and formula (11) compounds as described for Method A.

SCHEME II

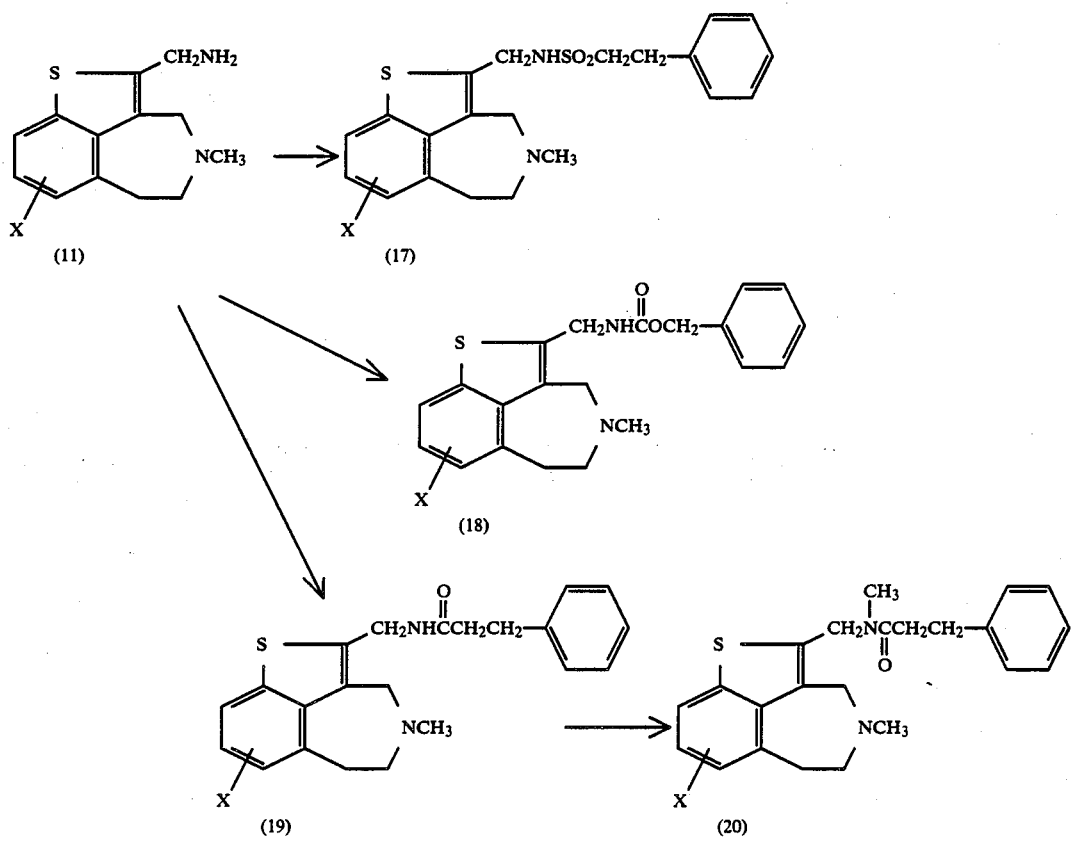

Scheme II shows the synthesis of Formula (I) compounds in which the 2—CH₂NH₂ moiety is substituted by a group Z, which is R, COR⁵, CONRR⁶, CO₂R², or SO₂R⁷. In Scheme II, X is as defined in Formula (I), the R group attached to the nitrogen of the azepine ring is represented by a methyl group. According to Scheme II, compounds of the types exemplified by formulas (17), (18), and (19) can be obtained from formula (11) compounds.

Formula (17) compounds are prepared by reacting formula (11) compounds with an appropriately substituted sulfonyl chloride, such as styryl sulfonyl chloride, in the presence of a base, such as triethylamine, in an inert solvent, for example, tetrahydrofuran, to prepare the desired sulfonamide derivatives (17).

Formula (18) compounds are prepared from formula (11) compounds by treatment with a suitable haloformate, for example benzylchloroformate or ethylchloroformate, in the presence of a base, such as triethylamine, in a suitable solvent, such as tetrahydrofuran.

Formula (19) compounds are prepared by reacting formula (11) compounds with an acid chloride, for example hydrocinnamoyl chloride or propionyl chloride, in the presence of a base, such as triethylamine, in an inert solvent, such as tetrahydrofuran.

Formula (17), (18), and (19) compounds are elaborated further to produce compounds which are more highly substituted on the nitrogen of the 2—CH₂NH₂ group. Formula (20) compounds are an example of this group of compounds. These products are formed when a formula (19) compound is alkylated by a C₁₋₆alkyl halide or a C₃₋₅alkenyl halide, such as methyliodide or allyl iodide, in the presence of a base, such as sodium hydride, in a suitable solvent, such as dimethylformamide.

SCHEME III

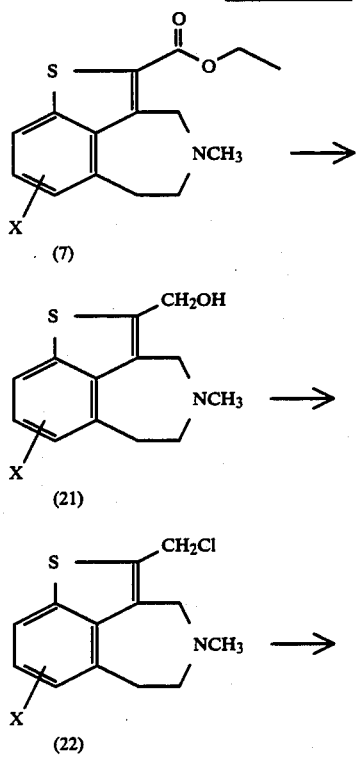

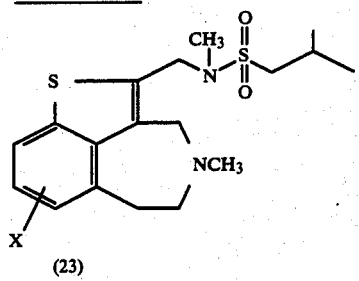

Scheme III shows an alternate route to the preparation of substituted 2-(sulfonamido)methyl Formula (I) compounds, which are Scheme II, formula (17) compounds. In Scheme III, X is as defined in Formula (I) and the R group attached to the nitrogen of the azepine ring is represented by a methyl group.

According to Scheme III, formula (7) compounds are added to a suitable reducing agent, preferably lithium aluminum hydride (LAH) and aluminum chloride, in an inert solvent, such as ethyl ether, to yield formula (21) compounds. Formula (22) compounds are prepared from formula (21) compounds by treatment with a suitable halogenating agent, such as thionyl chloride, in an inert solvent, such as methylene chloride. The halide in formula (22) compounds is displaced by an appropriately substituted sulfonamide, such as N,2-dimethyl-1-propanesulfonamide (synthesis described in U.S. Pat. No. 4,454,139), in the presence of a base, preferably sodium hydride, in a suitable solvent, such as dimethylformamide, to give formula (23) compound.

Schemes I through III outline preparation of Formula (I) compounds in which R is methyl. Formula (I) compounds wherein R is other than methyl are formed by selecting the N-(C₁₋₆alkyl)aminoacetaldehyde di(C₁₋₄alkyl)acetal used in preparing the formula (5) compounds of Scheme I, Method A, or formula (13) compounds of Scheme I, Method B, so that the nitrogen is desirably substituted. Alternatively, Formula (I) compounds wherein R is other than methyl are prepared by reacting a Formula (I) compound wherein R is methyl with an alkyl haloformate, preferably trichloroethyl chloroformate, at approximately 50° C. to 100° C. to produce a trihaloalkyl carbamate. To this carbamate dissolved in a suitable organic solvent, such as tetrahydrofuran, is added an acid, preferably acetic acid, and a reducing agent, such as zinc dust, to yield a product in which R is hydrogen. This subsequently is reacted with a halo-R⁸ compound, wherein R⁸ is C₂₋₆alkyl or C₃₋₅alkenyl, to yield Formula (I) compounds wherein R is C₂₋₆alkyl or C₃₋₅alkenyl, respectively.

The substituted thiophenols and C₁₋₄alkyl 2-halopropanones used as starting materials in Scheme I are commercially available or can be synthesized from available materials by known methods. Additionally, the reactants used in Schemes I through III are available or can be synthesized from available materials by known methods.

The pharmaceutically acceptable, nontoxic, acid addition salts having the utility of the free bases of Formula (I), are formed with inorganic or organic acids, by methods well known in the art. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

Because the compounds of Formula (I) are α-adrenoceptor antagonists they are useful in treating cardiovascular diseases in which changes in vascular resistance are desirable, including hypertension, pulmonary hypertension, congestive heart failure, myocardial ischemia, angina pectoris, and peripheral vascular disease. Formula (I) compounds also are useful in treating benign prostatic hypertrophy, diabetes, glaucoma, ocular hypertension, obesity, disorders of gastrointestinal motility, including colonic spasm, irritable bowel syndrome, and constipation, impotence, and central nervous system disorders such as depression and senile dementia. Additionally, the invented compounds are useful in treating diseases resulting from inappropriate platelet aggregation.

The α-adrenoceptor activity of certain compounds of the present invention was determined using the following in vitro systems.

Alpha$_1$ adrenoceptor antagonist activity was determined using the rabbit aorta. Male New Zealand White rabbits (2-4 Kg) were euthanized by cervical concussion. A 4 cm portion of the thoracic aorta was removed and placed in a dish of cold (10° C.) Krebs-Hensleit solution. The tissue was cleaned of fat and connective tissue and cut into segments of approximately 3 mm in length. These segments were suspended in 10 ml tissue baths via hangers constructed of 0.25 mm tungsten wire. One hanger was fixed to a support in the bath and the other was attached via silk thread to a force displacement transducer.

Tissue segments were equilibrated for 2 hours prior to drug testing, during which time basal tension was maintained at 2 gm. Tissues were washed at 30 minute intervals during this equilibration period. The Krebs-Hensleit solution contained cocaine (6μM) to block neuronal uptake and propranolol (1 μM) to block beta-adrenoceptors. Tissues were usually challenged once with norepinephrine (0.1 μM) during the equilibration period to check for viability.

A cumulative concentration-response curve to norepinephrine was obtained in each aortic segment. Following washout of norepinephrine, the α-adrenoceptor antagonist to be tested was added to the bath. After the tissue had been in contact with the antagonist for 30-60 minutes, the norepinephrine concentration response-curve was repeated in the presence of antagonist. The tissue was then washed again, and a tenfold higher concentration of antagonist added. Following equilibration (30-60 minutes), a third norepinephrine concentration-response curve was determined in the presence of the antagonist.

The receptor dissociation constant ($K_B$) for the antagonist was determined using the relationship $$K_B = \frac{\text{Antagonist Concentration}}{\text{Dose Ratio} - 1}$$

(Furchgott, R. F., *Handbook of Experimental Pharmacology*, eds. Eichler, et al., pp. 283-335 (Springer 1972)). The $K_B$ value obtained at each antagonist concentration was averaged to obtain a mean $K_B$ for each experiment.

Alpha$_2$ adrenoceptor antagonist activity of the compounds was determined using the isolated, superfused guinea pig left atrium. Briefly, the heart is removed from a pentobarbital-anesthetized male guinea pig. The left atrium is separated, dissected free of extraneous tissue and mounted in a 2 ml superfusion chamber. The tissue is paced at 30 pulse/minute and the sympathetic nerves excited at 6 minute intervals by field stimulation. The response to nerve stimulation is measured as the difference in contractile force between the basal contraction and peak contraction following a nerve stimulation. A concentration-response curve for B-HT 920 (a known $\alpha_2$ agonist) is prepared by administering increasing concentrations of B-HT 920 following each successive stimulation. The tissue then is superfused for thirty minutes with the α-adrenoceptor antagonist to be tested and the B-HT 920 concentration-effect curve is repeated in the presence of antagonist. Data are reported as $K_B$, defined above. Additional details of this test system are found in Hieble, J. P. and R. G. Pendleton, *Arch. Pharmacol.*, 309:217-224 (1979).

Alpha$_3$ adrenoceptor antagonist receptor activity was determined using the dog saphenous vein (DSV) as the test system. This test system has been shown a suitable preparation in which to characterize postsynaptic $\alpha_2$ ($\alpha_3$) adrenoceptors, Sullivan, A. T. and G. M. Drew, *Arch. Pharmacol.*, 314:249-58 (1980). This test system is prepared by removing the lateral saphenous vein from an anesthetized dog and cutting the vein into segments of 4 mm in length. Segments are mounted as described for the isolated rabbit aorta.

The $\alpha_3$ adrenoceptor antagonist activity of the compounds of interest is determined by measuring shifts in the dose-response curve of a specific agonist induced by the tested compounds. The $\alpha_2$, $\alpha_3$ agonist, B-HT 920, was used in testing the compounds listed in Table I.

Representative Formula (I) compounds which were tested using the above described in vitro test systems are listed in Table 1. Each of the compounds tested was found to have antagonist activity at one or more of the α-adrenoceptor subtypes.

TABLE 1

N-[(7-chloro-3,4,5,6-tetrahydro-4-methylthieno[4,3,2-ef][3]benzazepin-2-yl)methyl]-2-methylpropanesulfonamide;
7-chloro-3,4,5,6-tetrahydro-4-methylthieno[4,3,2-ef]-[3]benzazepine-2-methanamine;
N-[(7-chloro-3,4,5,6-tetrahydro-4-methylthieno[4,3,2-ef][3]benzazepin-2-yl)methyl]-2-phenylethenesulfonamide;
N-[(7-chloro-3,4,5,6-tetrahydro-4-methylthieno[4,3,2-ef][3]benzazepin-2-yl)methyl]-2-benzeneethanesulfonamide; and
N-[(7-chloro-3,4,5,6-tetrahydro-4-methylthieno[4,3,2-ef][3]benzazepin-2-yl)methyl]-2-benzenesulfonamide.

The antihypertensive activity of certain compounds of the present invention was determined using the spontaneously hypertensive rat model. The details of this in vivo test are found in Roesler, J. M., et al., *J. Pharmacol. Exp. Ther.*, 236:1-7 (1986).

When the compound of Example 7 is tested in spontaneously hypertensive rats following oral administration at 20 mg/kg, a dose related reduction in arterial blood pressure is observed.

Novel pharmaceutical compositions are obtained when the compounds are incorporated with pharmaceutical carriers into convenient dosage forms such as capsules, tablets, or injectable preparations. Standard solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid, or an aqueous or nonaqueous liquid suspension or solution.

The pharmaceutical preparations are made following conventional techniques of a pharmaceutical chemist involving mixing, granulating and compressing, when necessary, for tablet forms, or mixing, filling, and dissolving the ingredients, as appropriate, to give the desired oral or parenteral products.

Doses of the present compounds in pharmaceutical dosage units will be an efficacious, nontoxic quantity selected from the range of 0.01–100 mg/kg of active compound, preferably 0.1–50 mg/kg. The selected dose is administered to a human patient in need of treatment from 1–4 times daily, orally, rectally, topically, by inhalation, or injection, or continuously by infusion. Oral administration, however, is preferred because it is more convenient for the patient.

The following examples are illustrative of preparation of Formula (I) compounds. The examples are not intended to limit the scope of the invention as defined hereinabove and as claimed below.

EXAMPLE 1

Method A—Ethyl 7-Chloro-3,4,5,6-tetrahydro-4-methylthieno[4,3,2 ef][3]benzazepine-2-carboxylate (i) 1-[(4-Chlorophenyl)thio]-2-propanone Chloroacetone (32.3 g, 0.347 mol) was added to a mixture of 4-chlorothiophenol (50 g, 0.347 mol) and sodium hydroxide (14 g, 0.347 mol) in water (400 ml) and the mixture was stirred at 25° C. for 1 hour. The mixture was extracted with ethyl ether and the organic phase was washed with water, dried with magnesium sulfate and concentrated to give 68 g (98%) of 1-[(4-chlorophenyl)thio]-2-propanone.

(ii) 5-Chloro-3-methylbenzo[b]thiophene

1-[(4-Chlorophenyl)thio]-2-propanone (50 g, 0.25 mol) was added to polyphosphoric acid (300 g) and the mixture was stirred as the temperature was gradually raised to 120° C. as an exotherm started. The mixture was stirred at 130° C. for 1 hour, diluted with water, extracted with ethyl ether and the organic phase was dried and concentrated. The residue was stirred in methanol (200 ml), filtered and the filtrate concentrated to give 17.5 g (40%) of 5-chloro-3-methylbenzo[b]thiophene: bp 120° C. (0.6 mm).

(iii) Ethyl 5-Chloro-3-methylbenzo[b]thiophene-2-carboxylate

Butyllithium in hexane (2.6M, 2.3 ml) was added to a solution of 5-chloro-3-methylbenzo[b]thiophene (1.0 g, 6 mmol) in ethyl ether (20 ml) stirred at 0° C. under argon. The mixture was stirred for 30 minutes and transferred slowly under argon pressure to a stirred solution of ethyl chloroformate (0.63 g, 6 mmol) in ethyl ether (20 ml). The mixture was stirred at 0° C. for 30 minutes and at 25° C. for 1.5 hours. The mixture was treated with water and the organic phase was dried, concentrated and triturated with hexane to give 1.0 g (67%) of ethyl 5-chloro-3-methylbenzo[b]thiophene-2-carboxylate: mp 92.5°–94° C.

(iv) Ethyl 3-Bromomethyl-5-chlorobenzo[b]thiophene-2-carboxylate

A mixture of ethyl 5-chloro-3-methylbenzo[b]thiophene-2-carboxylate (9.0 g, 0.035 mol), N-bromosuccinimide (6.53 g, 0.037 mol) and benzoyl peroxide (130 mg) in carbon tetrachloride (150 ml) was refluxed and illuminated with a sunlamp for 2 hours. The resulting suspension was cooled, filtered and the filter cake was triturated with methanol to give 9.9 g (85%) of the methanol insoluble ethyl 3-bromomethyl-5-chlorobenzo[b]thiophene-2-carboxylate: mp 148°–150° C.

(v) Ethyl 5-Chloro-3-[N-(2,2-dimethoxyethyl)-N-methyl(aminomethyl)]benzo[b]thiophene-2-carboxylate A mixture of ethyl 3-bromomethyl-5-chlorobenzo[b]thiophene-2-carboxylate (11.0 g, 0.033 mol), methylaminoacetaldehyde dimethyl acetal (4.76 g, 0.04 mol) and potassium carbonate (11.4 g, 0.8 mol) in dry acetone (200 ml) was stirred for 48 hours, filtered and the filtrate concentrated to give 11.8 g (96%) of ethyl 5-chloro-3-[N-(2,2-dimethoxyethyl)-N-methyl-(aminomethyl)]benzo[b]thiophene-2-carboxylate.

(vi) Ethyl 7-Chloro-3,4-dihydro-4-methylthieno[4,3,2-ef][3]benzazepine-2-carboxylate Ethyl 5-chloro-3-[N-(2,2-dimethoxyethyl)-N-methyl-(aminomethyl)]benzo[b]thiophene-2-carboxylate (3.0 g, 8.1 mmol) was added in portions to trifluoromethanesulfonic acid (10 ml) stirred at 0° C. under argon. The mixture was stirred at 25° C. for 45 minutes and diluted with water. The mixture was basified with aqueous sodium hydroxide and extracted with ethyl ether to give ethyl 7-chloro-3,4-dihydro-4-methylthieno-[4,3,2-ef][3]benzazepine-2-carboxylate.

(vii) Ethyl 7-Chloro-3,4,5,6-tetrahydro-4-methylthieno[4,3,2-ef][3]benzazepine-2-carboxylate Diborane in tetrahydrofuran (1M, 40 ml) was added to a solution of ethyl 7 chloro-3,4-dihydro-4-methylthieno[4,3,2-ef][3]benzazepine-2-carboxylate (2.8 g) in tetrahydrofuran (30 ml) stirred at 0° C. The mixture was refluxed for 3 hours and stirred at 25° C. for 16 hours, cooled, treated with methanol (50 ml), refluxed for 18 hours and concentrated. The residue was triturated with ethyl ether-hexane (3:1) to give 1.6 g (64%) of ethyl 7-chloro-3,4,5,6 tetrahydro-4-methylthieno[4,3,2-ef][3]benzazepine-2-carboxylate: mp 138°–140° C. The free base was treated with hydrogen chloride to give ethyl 7-chloro-3,4,5,6-tetrahydro-4-methylthieno[4,3,2-ef][3]benzazepine-2-carboxylate hydrochloride: mp 240° C.

Method B—Methyl 7-Chloro-3,4,5,6-tetrahydro-4-methylthieno[4,3,2-ef][3]benzazepine-2-carboxylate (i) 3-Bromomethyl-5-chlorobenzo[b]thiophene Using the general procedure of Example 1, Method A, (iv), replacing ethyl-5-chloro-3-methylbenzo[b]thiophene-2-carboxylate with 5-chloro-3-methylbenzo[b]thiophene gave 2.78 g (57%) of 3-bromomethyl-5-chlorobenzo[b]thiophene: mp 126°–128° C.

(ii) 5-Chloro-3-[N-(2,2-dimethoxyethyl)-N-methyl-(aminomethyl)]benzo[b]thiophene Using the general procedure of Example 1, Method A, (v), replacing ethyl-3-bromomethyl-5-chlorobenzo[b]thiophene-2-carboxylate with 3-bromomethyl-5-chlorobenzo[b]thiophene gave 2.1 g (95%) of 5-chloro- 3-[N-(2,2-dimethoxyethyl)-N-methyl-(aminomethyl)-]benzo[b]thiophene.

(iii) 5-Chloro-3-[N-(2,2-dimethoxyethyl)-N-methyl-(aminomethyl)]benzo[b]thiophene-2-carboxylic Acid Butyllithium in tetrahydrofuran (2.6M, 0.04 mol) was added slowly to a solution of 5-chloro-3-[N-(2,2-dimethoxyethyl)-N-methyl(aminomethyl)]benzo[b]thiophene (10 g, 0.033 mol) in freshly distilled tetrahydrofuran (100 ml) stirred at −30° C. under argon. The mixture was stirred for 30 minutes, treated with dry carbon dioxide for 5 minutes and allowed to warm to 25° C. The mixture was treated with methanol, poured into ice water and extracted with ethyl ether. The aqueous phase was adjusted to pH 7.5 and extracted with methylene chloride. The organic phase was washed with water, dried with magnesium sulfate and concentrated to give 6.0 g (54%) of 5-chloro-3-[N-(2,2-dimethoxyethyl)-N-methyl(aminomethyl)]benzo[b]thiophene-2-carboxylic acid.

(iv) Methyl-5-Chloro-3-[N-(2,2-dimethoxyethyl)-N-methyl(aminomethyl)]benzo[b]thiophene-2-carboxylate A suspension of 5-chloro-3-[N-(2,2-dimethoxyethyl)-N-methyl(aminomethyl)]benzo[b]thiophene-2-carboxylic acid (5.0 g, 14.5 mmol) in methylene chloride-tetrahydrofuran was stirred at 0° C. and treated with excess diazomethane in ethyl ether. The mixture was stirred for 2 hours at 0° C., treated with a stream of argon and concentrated to give 5.0 g (96%) of methyl-5-chloro-3-[N-(2,2-dimethoxyethyl)-N-methyl(aminomethyl)]benzo[b]thiophene-2-carboxylate.

(v) Methyl-7-Chloro-3,4-dihydro-4-methylthieno[4,3,2-ef][3]benzazepine-2-carboxylate Using the general procedure of Example 1, Method A, (vi), replacing ethyl-5-chloro-3-[N-(2,2-dimethoxyethyl)-N-methyl(aminomethyl)]benzo[b]thiophene-2-carboxylate with methyl-5-chloro-3-[N-(2,2-dimethoxyethyl)-N-methyl(aminomethyl)]benzo[b]thiophene-2-carboxylate gave methyl-7-chloro-3,4-dihydro-4-methylthieno[4,3,2-ef][3]benzazepine-2-carboxylate.

(vi) Methyl-7-Chloro-3,4,5,6-tetrahydro-4-methylthieno[4,3,2-ef][3]benzazepine-2-carboxylate A solution of methyl 7-chloro-3,4-dihydro-4-methylthieno[4,3,2-ef][3]benzazepine-2-carboxylate in ethanol (30 ml) containing platinum oxide (0.3 g) was shaken under hydrogen (30 psi) for 2 hours. The mixture was filtered, concentrated and treated with ethereal hydrogen chloride to give methyl 7-chloro-3,4,5,6-tetrahydro-4-methylthieno[4,3,2-ef][3]benzazepine-2-carboxylate hydrochloride: mp 215°–216° C.

EXAMPLE 2

7-Chloro-3,4,5,6-tetrahydro-4-methylthieno[4,3,2-ef][3]benzazepine-2-methanol

To a mechanically stirred mixture of lithium aluminum hydride (1.95 g, 49 mmol) in freshly distilled tetrahydrofuran at 0° C. was added over 5 minutes a solution of ethyl 7-chloro-3,4,5,6-tetrahydro-4-methylthieno[4,3,2-ef][3]benzazepine-2-carboxylate (5 g, 15.5 mmol), prepared as in Example 1, Method A, in tetrahydrofuran (30 ml). The resulting white suspension was stirred for 11.5 hours and then water (2 ml), a solution of 10% sodium hydroxide (4 ml), and water (7.8 ml) were sequentially added dropwise at 0° C. The mixture was stirred for 10 minutes and the white precipitate was filtered. The filtrate was evaporated and pumped down to give a yellow solid (4.4 g) which was triturated with cold methanol (16 ml) and filtered to give 7-chloro-3,4,5,6-tetrahydro-4-methylthieno[4,3,2-ef][3]benzazepine-2-methanol (2.4 g, 57%, mp 98°–100° C.).

EXAMPLE 3

2-Chloromethyl-7-chloro-3,4,5,6-tetrahydro-4-methylthieno[4,3,2-ef][3]benzazepine To a suspension of 7-chloro-3,4,5,6-tetrahydro-4-methylthieno[4,3,2-ef][3]benzazepine-2-methanol (1.0 g, 3.9 mmol), prepared as in Example 2, in methylene chloride (50 ml) at 0° C. was added thionyl chloride (50 ml) over 5 minutes. After 20 minutes, the mixture was evaporated and pumped down to give 2-chloromethyl-7-chloro-3,4,5,6-tetrahydro-4-methylthieno[4,3,2-ef][3]benzazepine hydrochloride (1.28 g, 99%).

EXAMPLE 4

7-Chloro-3,4,5,6-tetrahydro-4-methylthieno[4,3,2-ef][3]benzazepine-2-carbonyl Chloride A mixture of ethyl-7-chloro-3,4,5,6-tetrahydro-4-methylthieno[4,3,2-ef][3]benzazepine-2-carboxylate (15 g, 46.4 mmol), prepared as in Example 1, Method A, in glacial acid (240 ml) and 6N hydrochloric acid (240 ml) was refluxed with stirring for 5 hours. The mixture was stirred at room temperature overnight. A white solid precipitated from the reaction mixture and this was filtered to give the carboxylic acid hydrochloride (13.5 g), which was refluxed in thionyl chloride (100 ml) for 2.5 hours. The reaction solution was concentrated to remove the thionyl chloride and the residue was azeotroped with toluene to give 7-chloro-3,4,5,6-tetrahydro-4-methylthieno[4,3,2-ef][3]benzazepine-2-carbonyl chloride (14 g, 97%, mp 270° C. dec).

EXAMPLE 5

7-Chloro-3,4,5,6-tetrahydro-4-methylthieno[4,3,2-ef][3]benzazepine-2-carboxamide To a stirring ammonium hydroxide solution saturated with anhydrous ammonia gas was added 7-chloro-3,4,5,6-tetrahydro-4-methylthieno[4,3,2-ef][3]benzazepine-2-carbonyl chloride (10 g, 32 mmol), prepared as in Example 4, for 1 hour. The suspension was filtered to give 7-chloro-3,4,5,6-tetrahydro-4-methylthieno[4,3,2-ef][3]benzazepine-2-carboxamide (6 g, 67%, mp 203°–204° C.).

EXAMPLE 6

7-Chloro-3,4,5,6-tetrahydro-4-methylthieno[4,3,2-ef][3]benzazepine-2-methanamine To a solution of 7-chloro-3,4,5,6-tetrahydro-4-methylthieno[4,3,2-ef][3]benzazepine-2-carboxamide (0.5 g, 1.8 mmol), prepared as in Example 5, in tetrahydrofuran (10 ml) was added a solution (1M in tetrahydrofuran) of diborane (5 ml, 5 mmol). The mixture was refluxed for 3 hours, then treated with methanol (10 ml) and dilute hydrochloric acid (2 ml). The mixture was refluxed for 30 minutes and allowed to stir at room temperature overnight. The product precipitated out of the mixture and was filtered to give 7-chloro-3,4,5,6-tetrahydro-4-methylthieno[4,3,2-ef][3]benzazepine-2-methanamine hydrochloride (0.3 g, 63%, mp >290° C.).

EXAMPLE 7

N-[(7-Chloro-3,4,5,6-tetrahydro-4-methylthieno[4,3,2-ef][3]benzazepin-2-yl)methyl]2-methylpropanesulfonamide To a magnetically stirred solution of N,2-dimethyl-1 propanesulfonamide (0.49 g, 3.2 mmol, U.S. Pat. No. 4,454,139) in dimethylformamide (16 ml) was added slowly a 50% dispersion of sodium hydride (0.35 g, 7.3 mmol) in mineral oil. After the hydrogen gas evolution had subsided, 2-chloromethyl-7-chloro-3,4,5,6-tetrahydro-4-methylthieno[4,3,2-ef][3]benzazepine hydrochloride (0.79 g, 2.45 mmol), prepared as in Example 3, was added in portions and rinsed with more dimethylformamide (30 ml). The resulting mixture was stirred for 1 hour at room temperature, poured into ice-water (300 ml) and saturated sodium chloride (50 ml), then extracted with ethyl acetate. The combined extracts were washed with water, saturated sodium chloride solution, and dried over magnesium sulfate. The residue (1.1 g) obtained after evaporation was taken up in ethyl acetate and treated with activated carbon and filtered. The filtrate was concentrated to a 4-ml volume and chilled and the resulting crystals were filtered to give N-[(7-chloro-3,4,5,6-tetrahydro-4-methylthieno[4,3,2-ef][3]benzazepin-2-yl)methyl]-2-methylpropanesulfonamide (0.48 g, 49%, mp 107°–108° C.).

EXAMPLE 8

N-[(7-Chloro-3,4,5,6-tetrahydro-4-methylthieno[4,3,2-ef][3]benzazepin 2-yl)methyl-]-2-phenylethenesulfonamide To a magnetically stirred solution of 7-chloro-3,4,5,6-tetrahydro-4-methylthieno[4,3,2-ef][3]benzazepine-2-methanamine hydrochloride (0.5 g, 1.5 mmol), prepared as in Example 6, and triethylamine (2.5 ml) in tetrahydrofuran (25 ml) at 5° C. was added slowly a solution of styryl sulfonyl chloride (0.324 g, 1.6 mmol) in tetrahydrofuran (2.5 ml). The resulting mixture was stirred for 2 hours at room temperature, poured into a cold solution of sodium bicarbonate (8 ml), and extracted with methylene chloride. The combined extracts were washed with water, saturated sodium chloride solution, and dried over magnesium sulfate. The residue (0.4 g) obtained after evaporation was taken up in ethyl acetate and chilled and the resulting solid was filtered to give N-[(7-chloro-3,4,5,6-tetrahydro-4-methylthieno[4,3,2-ef][3]benzazepin-2-yl)methyl]-2-phenylethenesulfonamide (0.1 g, 15%, mp 155°–157° C.).

EXAMPLE 9

N-[(7-Chloro-3,4,5,6-tetrahydro-4-methylthieno[4,3,2-ef][3]benzazepin-2-yl)methyl]-2-benzeneethanesulfonamide To a magnetically stirred solution of 7-chloro-3,4,5,6-tetrahydro-4-methylthieno[4,3,2-ef][3]benzazepine-2-methanamine hydrochloride (0.5 g, 1.5 mmol), prepared as in Example 6, and triethylamine (2.5 ml) in tetrahydrofuran (25 ml) at 5° C. was added slowly a solution of 2-phenethyl sulfonyl chloride (0.324 g, 1.6 mmol) in tetrahydrofuran (2.5 ml). The resulting mixture was stirred for 2 hours at room temperature, poured into a cold solution of sodium bicarbonate (8 ml), and extracted with methylene chloride. The combined extracts were washed with water, saturated sodium chloride solution, and dried over magnesium sulfate. The residue obtained after evaporation was flash chromatographed on silica gel to give N-[(7-chloro-3,4,5,6-tetrahydro-4-methylthieno[4,3,2-ef][3]benzazepin-2-yl)methyl]-2-benzeneethanesulfonamide (0.152 g, 23%, mp 135° C.).

EXAMPLE 10

N-[(7-chloro-3,4,5,6-tetrahydro-4-methylthieno[4,3,2-ef][3]benzazepin-2-yl)methyl]-2-benzenesulfonamide To a magnetically stirred solution of 7-chloro-3,4,5,6-tetrahydro-4-methylthieno[4,3,2-ef][3]benzazepine-2-methanamine hydrochloride (0.4 g, 1.2 mmol), prepared as in Example 6, and triethylamine (2 ml) in tetrahydrofuran (25 ml) at 5° C. was added slowly a solution of benzene sulfonyl chloride (0.265 g, 1.5 mmol) in tetrahydrofuran (2.5 ml). The resulting mixture was stirred for 2 hours at room temperature, poured into a cold solution of sodium bicarbonate (8 ml), and extracted with methylene chloride. The combined extracts were washed with water, saturated sodium chloride solution, and dried over magnesium sulfate. The residue obtained after evaporation slowly crystallized and was triturated with diethyl ether to give N-[(7-chloro-3,4,5,6-tetrahydro-4-methylthieno[4,3,2-ef][3]benzazepin-2-yl)methyl]-2-benzenesulfonamide (0.2 g, 41%, mp 186° C.).

EXAMPLE 11

N-[(7-Chloro-3,4,5,6-tetrahydro-4-methylthieno[4,3,2-ef][3]benzazepin-2-yl)methyl]benzenepropanamide To a solution of 7-chloro-3,4,5,6-tetrahydro-4-methylthieno[4,3,2-ef][3]benzazepine-2-methanamine hydrochloride (2.0 mmol), prepared as in Example 6, and triethylamine (1.1 ml, 7.9 mmol) in tetrahydrofuran (6 ml) at 0°–5° C. is added dropwise over 5 minutes a solution of hydrocinnamoyl chloride (0.3 ml, 1.98 mmol). The reaction mixture is stirred in an ice bath for 30 minutes and quenched with ice cold 5% sodium bicarbonate solution (80 ml). The product is extracted into ethyl acetate. Evaporation of the extract gives N-[(7-chloro-3,4,5,6-tetrahydro-4-methylthieno[4,3,2-ef][3]benzazepin-2-yl)methyl]benzenepropanamide.

EXAMPLE 12

N-[(7-Chloro-3,4,5,6-tetrahydro-4-methylthieno[4,3,2-ef][3]benzazepin-2-yl)methyl]-2-phenoxyacetamide To a suspension of 7-chloro-3,4,5,6-tetrahydro-4-methylthieno[4,3,2-ef][3]benzazepine-2-methanamine hydrochloride (1.77 mmol), prepared as in Example 6, and triethylamine (1 ml) in tetrahydrofuran (25 ml) in an ice bath is added dropwise phenoxyacetyl chloride (0.28 ml, 2.0 mmol). After removing the ice bath, the mixture is allowed to stir overnight at room temperature. The reaction is quenched with ice-water and the product is extracted with ethyl ether. The extract is dried over magnesium sulfate and evaporated to give N-[(7-chloro-3,4,5,6-tetrahydro-4-methylthieno[4,3,2-ef][3]benzazepin-2-yl)methyl]-2-phenoxyacetamide.

EXAMPLE 13

N-[(7-Chloro-3,4,5,6-tetrahydro-4-methylthieno[4,3,2-ef][3]benzazepin-2-yl)methyl]carbamic Acid Phenylmethyl Ester To a solution of 7-chloro-3,4,5,6-tetrahydro-4-methylthieno[4,3,2-ef][3]benzazepine-2-methanamine hydrochloride (2.0 mmol), prepared as in Example 6, and triethylamine (1.1 ml) in tetrahydrofuran (6.0 ml) in an ice-bath is added dropwise over 4 minutes a solution of benzyl chloroformate (0.29 ml, 1.93 mmol) in tetrahydrofuran (2 ml). The reaction mixture is stirred for 40 minutes, quenched with cold 5% sodium bicarbonate solution (80 ml), and extracted with ethyl acetate. The extract is washed with saturated sodium chloride solution, dried over sodium sulfate and evaporated to give N-[(7-chloro-3,4,5,6-tetrahydro-4-methylthieno[4,3,2-ef][3]benzazepin-2-yl)methyl]carbamic acid phenylmethyl ester.

EXAMPLE 14

N-[(7-Chloro-3,4,5,6-tetrahydro-4-methylthieno[4,3,2-ef][3]benzazepin-2-yl)methyl]carbamic Acid Ethyl Ester To a magnetically stirred solution of 7-chloro-3,4,5,6-tetrahydro-4-methylthieno[4,3,2-ef][3]benzazepine-2-methanamine hydrochloride (3.0 mmol), prepared as in Example 6, and triethylamine (1.7 ml) in tetrahydrofuran (10 ml) at 5° C. is added slowly ethyl chloroformate (0.3 ml, 3.0 mmol). After 0.5 hours, the mixture is quenched with 5% sodium bicarbonate solution (100 ml) and extracted with ethyl acetate (2×50 ml). The combined organic extracts are washed with water and saturated sodium chloride solution, dried over magnesium sulfate, and evaporated to give N-[(7-chloro-3,4,5,6-tetrahydro-4-methylthieno[4,3,2-ef][3]benzazepin-2-yl)methyl]carbamic acid ethyl ester.

EXAMPLE 15

N-[(7-Chloro-3,4,5,6-tetrahydro-4-methylthieno4,3,2-ef][3]benzazepin-2-yl)methyl]-N-methyl carbamic Acid Ethyl Ester A solution of N-[(7-chloro-3,4,5,6-tetrahydro-4-methylthieno[4,3,2-ef][3]benzazepin-2-yl)methyl]carbamic acid ethyl ester (2.1 mmol), prepared as in Example 14, in dimethylformamide (6 ml) is treated with sodium hydride (50% dispersed in oil, 0.2 g, 4.2 mmol) at 0° C. A solution of iodomethane (0.14 g, 2.2 mmol) in dimethylformamide (1 ml) is then added. The resulting mixture is stirred in an ice bath for 15 minutes, quenched with a cold 5% sodium bicarbonate solution (100 ml), and extracted with a solution of ethyl acetate and hexane (75/15=v/v, 2×50 ml). The combined extracts are washed with water (2×15 ml) and saturated sodium chloride solution (1×15 ml), dried over magnesium sulfate, and dried over magnesium sulfate, and evaporated to give N-[(7-chloro-3,4,5,6-tetrahydro-4-methylthieno[4,3,2-ef][3]benzazepin-2-yl)methyl]-N-methyl carbamic acid ethyl ester.

EXAMPLE 16

N-[(7-Chloro-3,4,5,6-tetrahydro-4-methylthieno[4,3,2-ef][3]benzazepin-2-yl)methyl]propanamide To a magnetically stirred solution of 7-chloro-3,4,5,6-tetrahydro-4-methylthieno[4,3,2-ef][3]benzazepine-2-methanamine hydrochloride (3.2 mmol), prepared as in Example 6, and triethylamine (1.8 ml, 12.4 mmol) in tetrahydrofuran (12 ml) at 5° C. is added slowly a solution of propionyl chloride (0.29 ml, 3.28 mmol) in tetrahydrofuran (3 ml) at 5° C. The resulting mixture is stirred for 1 hour, poured into a cold solution of sodium bicarbonate, and extracted with ethyl acetate. The extract is washed with water, saturated sodium chloride solution, and dried over magnesium sulfate. The residue obtained after evaporation is purified by flash chromatography to give N-[(7-chloro-3,4,5,6-tetrahydro-4-methylthieno[4,3,2-ef][3]benzazepin-2-yl)methyl]propanamide.

EXAMPLE 17

N-[(7-Chloro-3,4,5,6-tetrahydro-4-methylthieno[4,3,2-ef][3]benzazepin-2-yl)methyl]-N-methyl-propanamide To a stirred solution of N-[(7-chloro-3,4,5,6-tetrahydro-4-methylthieno[4,3,2-ef][3]benzazepin-2-yl)methyl]propanamide (1.4 mmol), prepared as in Example 16, in dimethylformamide (8 ml) under argon is added sodium hydride dispersed in mineral oil (0.1 g, 2.3 mmol) at room temperature. After 15 minutes, the reaction mixture is cooled to 0° C. and a solution of iodomethane (0.1 ml, 1.3 mmol) is added over 5 minutes. The mixture is poured into a cold solution of sodium bicarbonate and saturated sodium chloride. The aqueous phase is extracted with ethyl acetate, dried over magnesium sulfate, and evaporated to give N-[(7-chloro-3,4,5,6-tetrahydro-4-methylthieno[4,3,2-ef][3]benzazepin-2-yl)methyl]-N-methyl-propanamide.

EXAMPLE 18

N-[(7-Chloro-3,4,5,6-tetrahydro-4-methylthieno[4,3,2-ef][3]benzazepin-2-yl)methyl]benzamide To a magnetically stirred solution of 7-chloro-3,4,5,6-tetrahydro-4-methylthieno[4,3,2-ef][3]benzazepine-2-methanamine hydrochloride (1.0 mmol), prepared as in Example 6, and triethylamine (0.43 ml, 3.1 mmol) in methylene chloride (3 ml) at 5° C. is added slowly a solution of benzoyl chloride (0.15 ml, 1.3 mmol) in methylene chloride (2.5 ml) at 5° C. The resulting mixture is stirred for 2 hours at room temperature, poured into a cold solution of sodium bicarbonate (8 ml), and extracted with methylene chloride. The combined extracts are washed with water, saturated sodium chloride solution, and dried over magnesium sulfate. The residue obtained after evaporation is purified by flash chromatography to give N-[(7-chloro-3,4,5,6-tetrahydro-4-methylthieno[4,3,2-ef][3]benzazepin-2-yl)methyl]benzamide.

EXAMPLE 19

7-Chloro-3,4,5,6-tetrahydro-N,N,4-trimethyl-thieno[4,3,2-ef][3]benzazepine-2-carboxamide To a mixture of 7-chloro-3,4,5,6-tetrahydro-4-methylthieno[4,3,2-ef][3]benzazepine-2-carbonyl chloride (0.62 mmol), prepared as in Example 4, in methylene chloride (30 ml) at 0° C. is bubbled dimethylamine for 5 minutes. The resulting solution is stirred for one hour, washed with 10% sodium hydroxide solution and dried over magnesium sulfate. Removal of the solvent gives 7-chloro-3,4,5,6-tetrahydro-N,N,4-trimethyl-thieno[4,3,2-ef][3]benzazepine-2-carboxamide.

EXAMPLE 20

7-Methyl-3,4,5,6-tetrahydro-4-methylthieno[4,3,2-ef][3]benzazepine-2-methanamine Using the general procedure of Example 1, Method A, replacing 4-chlorophenol with 4-methylphenol gives ethyl 7-methyl-3,4,5,6-tetrahydro-4-methylthieno[4,3,2-ef][3]benzazepine-2-carboxylate.

Using the general procedures of Examples 4, 5, and 6, the ethyl 7-methyl carboxylate is de-esterified with hydrochloric acid in acetic acid, converted to an acid chloride with thionyl chloride, aminated with ammonia gas, and reduced with diborane to give 7-methyl- 3,4,5,6tetrahydro-4-methylthieno[4,3,2-ef][3]benzazepine-2-methanamine.

EXAMPLE 21

N-[(7-Methyl-3,4,5,6-tetrahydro-4-methylthieno[4,3,2-ef][3]benzazepin-2 yl)methyl]benzenepropanamide Using the general procedure of Example 11, replacing 7-chloro-3,4,5,6-tetrahydro-4-methylthieno[4,3,2-ef][3]benzazepine-2-methanamine with 7-methyl-3,4,5,6-tetrahydro-4-methylthieno[4,3,2-ef][3]benzazepine-2-methanamine, prepared as in Example 20, gives N-[(7-methyl-3,4,5,6-tetrahydro-4-methylthieno[4,3,2-ef][3]benzazepin-2-yl)methyl]benzenepropanamide.

EXAMPLE 22

N-[(7-Methyl-3,4,5,6-tetrahydro-4-methylthieno[4,3,2-ef][3]benzazepin-2-yl)methyl]carbamic Acid Phenylmethyl Ester Using the general procedure of Example 13, replacing chloro-3,4,5,6-tetrahydro-4-methylthieno[4,3,2-ef][3]benzazepine-2-methanamine with 7-methyl-3,4,5,6-tetrahydro-4-methylthieno[4,3,2-ef][3]benzazepine-2-methanamine, prepared as in Example 20, gives benzyl N-[(7-methyl-3,4,5,6-tetrahydro-4-methylthieno[4,3,2-ef][3]benzazepinyl)methyl]carbamic acid phenylmethyl ester.

EXAMPLE 23

N-[(7-Methyl-3,4,5,6-tetrahydro-4-methylthieno[4,3,2-ef][3]benzazepin-2-yl)methyl]-2-phenylethenesulfonamide Using the general procedure of Example 8, replacing 7-chloro-3,4,5,6-tetrahydro-4-methylthieno[4,3,2-ef][3]benzazepine-2-methanamine with 7-methyl-3,4,5,6-tetrahydro-4-methylthieno[4,3,2-ef][3]benzazepine-2-methanamine, prepared as in Example 20, gives N-[(7-methyl-3,4,5,6-tetrahydro-4-methylthieno[4,3,2-ef][3]benzazepin-2-yl)methyl]-2-phenylethenesulfonamide.

EXAMPLE 24

9-Chloro-3,4,5,6-tetrahydro-4-methylthieno[4,3,2-ef][3]benzazepine-2-methanamine Using the general procedure of Example 1, Method A, replacing 4-chlorophenol with 2-chlorophenol gives ethyl 9-chloro-3,4,5,6-tetrahydro-4-methylthieno[4,3,2-ef][3]benzazepine-2-carboxylate.

Using the general procedures of Examples 4, 5, and 6, ethyl 9-chloro-3,4,5,6-tetrahydro-4-methylthieno[4,3,2-ef][3]benzazepine-2-carboxylate is de-esterified, converted to an acid chloride, aminated, and reduced to give 9-chloro-3,4,5,6-tetrahydro-4-methylfuro[4,3,2-ef][3]benzazepine-2-methanamine.

EXAMPLE 25

N-[(9-Chloro-3,4,5,6-tetrahydro-4-methylthieno[4,3,2-ef][3]benzazepin-2-yl)methyl]benzenepropanamide Using the general procedure of Example 11, replacing 7-chloro-3,4,5,6-tetrahydro-4-methylthieno[4,3,2-ef][3]benzazepine-2-methanamine with 9-chloro-3,4,5,6-tetrahydro-4-methylthieno[4,3,2-ef][3]benzazepine-2-methanamine, prepared as in Example 24, gives N-[(9-chloro-3,4,5,6-tetrahydro-4-methylthieno[4,3,2-ef][3]benzazepin-2-yl)methyl]benzenepropanamide.

EXAMPLE 26

N-[(9-Chloro-3,4,5,6-tetrahydro-4-methylthieno[4,3,2-ef][3]benzazepin-2-yl)methyl]carbamic Acid Phenylmethyl Ester Using the general procedure of Example 13, replacing 7-chloro-3,4,5,6-tetrahydro-4-methylthieno[4,3,2-ef][3]benzazepine-2-methanamine with 9-chloro-3,4,5,6-tetrahydro-4-methylthieno[4,3,2-ef][3]benzazepine-2-methanamine, prepared as in Example 24, gives N-[(9-chloro-3,4,5,6-tetrahydro-4-methylthieno[4,3,2-ef][3]benzazepin-2-yl)methyl]carbamic acid phenylmethyl ester.

EXAMPLE 27

N-[(9-Chloro-3,4,5,6-tetrahydro-4-methylthieno[4,3,2-ef][3]benzazepin-2-yl)methyl]-2-phenylethenesulfonamide Using the general procedure of Example 8, replacing 7-chloro-3,4,5,6-tetrahydro-4-methylthieno[4,3,2-ef][3]benzazepine-2-methanamine with 9-chloro-3,4,5,6-tetrahydro-4-methylthieno[4,3,2-ef][3]benzazepine-2-methanamine, prepared as in Example 24, gives N-[(9-chloro-3,4,5,6-tetrahydro-4-methylthieno[4,3,2-ef][3]benzazepin-2-yl)methyl]-2-phenylethenesulfonamide.

EXAMPLE 28

7,9-Dichloro-3,4,5,6-tetrahydro-4-methylthieno[4,3,2-ef][3]benzazepine-2-methanamine Using the general procedure of Example 1, Method A, replacing 4-chlorophenol with 2,4-dichlorophenol yields ethyl 7,9-dichloro-3,4,5,6-tetrahydro-4-methylthieno[4,3,2-ef][3]benzazepine-2-carboxylate.

Using the general procedures of Examples 4, 5, and 6, ethyl 7,9-dichloro-3,4,5,6-tetrahydro-4-methylthieno[4,3,2-ef][3]benzazepine-2-carboxylate is de-esterified, converted to an acid chloride, aminated, and reduced to give 7,9-dichloro-3,4,5,6-tetrahydro-4-methylthieno[4,3,2-ef][3]benzazepine-2-methanamine.

EXAMPLE 29

N-[(7,9-Dichloro-3,4,5,6-tetrahydro-4-methylthieno[4,3,2-ef][3]benzazepin-2-yl)methyl]benzenepropanamide Using the general procedure of Example 11, replacing 7-chloro-3,4,5,6-tetrahydro-4-methylthieno[4,3,2-ef][3]benzazepine-2-methanamine with 7,9-dichloro-3,4,5,6-tetrahydro-4-methylthieno[4,3,2-ef][3]benzazepine-2-methanamine, prepared as in Example 28, gives N-[(7,9-dichloro-3,4,5,6-tetrahydro-4-methylthieno[4,3,2-ef][3]benzazepin-2-yl)methyl]benzenepropanamide.

EXAMPLE 30

N-[(7,9-Dichloro-3,4,5,6-tetrahydro-4-methylthieno[4,3,2-ef][3]benzazepin-2-yl)methyl]carbamic Acid Phenylmethyl Ester Using the general procedure of Example 13, replacing 7-chloro-3,4,5,6-tetrahydro-4-methylthieno[4,3,2-ef][3]benzazepine-2-methanamine with 7,9-dichloro-3,4,5,6-tetrahydro-4-methylthieno[4,3,2-ef][3]benzazepine-2-methanamine, prepared as in Example 28, gives benzyl N-[(7,9-dichloro-3,4,5,6-tetrahydro-4-methylthieno[4,3,2-ef][3]benzazepin-2-yl)methyl]carbamic acid phenylmethyl ester.

EXAMPLE 31

N-[(7,9-Dichloro-3,4,5,6-tetrahydro-4-methyl-thieno[4,3,2-ef][3]benzazepin-2-yl)methyl]-2-phenylethenesulfonamide Using the general procedure of Example 8, replacing 7-chloro-3,4,5,6-tetrahydro-4-methylthieno[4,3,2-ef][3]benzazepine-2-methanamine with 7,9-dichloro-3,4,5,6-tetrahydro-4-methylthieno[4,3,2-ef][3]benzazepine-2-methanamine, prepared as in Example 28, gives N-[(7,9-dichloro-3,4,5,6-tetrahydro-4-methylthieno[4,3,2-ef][3]benzazepin-2-yl)methyl]-2-phenylethenesulfonamide.

EXAMPLE 32

7-Chloro-3,4,5,6-tetrahydro-4-methylthieno[4,3,2-ef][3]benzazepine-2-acetonitrile To an ice cold solution of 2 chloromethyl 7-chloro-3,4,5,6-tetrahydro-4-methylthieno[4,3,2-ef][3]benzazepine hydrochloride, prepared as in Example 3, (2.16 mmol) in dimethyl sulfoxide (12 ml) is added triethylamine (0.5 ml). Sodium cyanide (3.0 mmol) is then added in one portion. The resulting mixture is heated at 50° C. for 2 hours and quenched with ice-water (70 ml) and extracted with ethyl acetate. The combined extracts are washed with water, saturated sodium chloride solution, and dried over magnesium sulfate. The residue obtained after evaporation is purified by flash chromatography on silica to give chloro-3,4,5,6-tetrahydro-4-methylthieno[4,3,2-ef][3]benzazepine-2-acetonitrile.

EXAMPLE 33

7-Chloro-3,4,5,6-tetrahydro-4-methylthieno[4,3,2-ef][3]benzazepine-2-ethanamine

To a suspension of lithium aluminum hydride (176 mmol) in anhydrous diethyl ether (200 ml) and tetrahydrofuran (50 ml) in an ice bath is added dropwise a solution of 7-chloro-3,4,5,6-tetrahydro-4-methyl-thieno[4,3,2-ef][3]benzazepine-2-acetonitrile (44 mmol), prepared as in Example 33, in anhydrous diethyl ether (200 ml) and tetrahydrofuran (50 ml). The resulting suspension is stirred at reflux for 6 hours, and then, water (7 ml), a solution of 10% sodium hydroxide (7 ml), and water (21 ml) are added sequentially. The mixture is diluted with ether (500 ml) and filtered. The filtrate is evaporated to give 7-chloro-3,4,5,6-tetrahydro-4-methylthieno[4,3,2-ef][3]benzazepine-2-ethanamine.

EXAMPLE 34

N-[2-(7-Chloro-3,4,5,6-tetrahydro-4-methylthieno-[4,3,2-ef][3]benzazepin-2-yl)ethyl]benzeneethanesulfonamide To a solution of 7-chloro-3,4,5,6-tetrahydro-4-methylthieno[4,3,2-ef][3]benzazepine-2-ethanamine (1.5 mmol), prepared as in Example 34, and triethylamine (2.5 ml) in tetrahydrofuran (25 ml) at 5° C. is added slowly a solution of 2-phenethyl sulfonyl chloride (1.6 mmol) in tetrahydrofuran (2.5 ml). The resulting mixture is stirred for 2 hours at room temperature, poured into a cold solution of sodium bicarbonate (8 ml), and extracted with methylene chloride. The combined extracts are washed with water, saturated sodium chloride solution, and dried over magnesium sulfate. The residue obtained after evaporation is flash chromatographed to give N-[2-(7-chloro-3,4,5,6-tetrahydro-4-methyl-thieno[4,3,2-ef][3]benzazepin-2-yl)ethyl]benzeneethanesulfonamide.

EXAMPLE 35

7-Chloro-3,4,5,6-tetrahydro-α,4-methylthieno[4,3,2-ef][3]benzazepine-2-acetonitrile To a solution of lithium diisopropylamide (2.6 mmol) in tetrahydrofuran (20 ml) at 78° C. is added dropwise a solution of 7-chloro-3,4,5,6-tetrahydro-4-methyl-thieno[4,3,2-ef][3]benzazepine-2-acetonitrile, prepared as in Example 33, in tetrahydrofuran. After 0.5 hours, a solution of iodomethane (0.18 ml) in tetrahydrofuran (4 ml) is added. The resulting mixture is warmed to room temperature of 1.5 hours, quenched with ice water, and extracted with ethyl ether. The combined extracts are washed with water, dried over magnesium sulfate, filtered, and concentrated to give 7-chloro-3,4,5,6-tetrahydro-α,4-methylthieno[4,3,2-ef][3]benzazepine-2-acetonitrile.

EXAMPLE 36

7-Chloro-3,4,5,6-tetrahydro-α,4-methylthieno[4,3,2-ef][3]benzazepine-2-ethanamine To a suspension of lithium aluminum hydride (176 mmol) in anhydrous diethyl ether (200 ml) and tetrahydrofuran (50 ml) in an ice bath is added dropwise a solution of 7-chloro-3,4,5,6-tetrahydro-α,4-methyl-thieno[4,3,2-ef][3]benzazepine-2-acetonitrile (44 mmol) in anhydrous diethyl ether (200 ml) and tetrahydrofuran (50 ml). The resulting suspension is stirred at reflux for 6 hours, and then, water (7 ml), a solution of 10% sodium hydroxide (7 ml), and water (21 ml) are added sequentially. The mixture is diluted with ether (500 ml) and filtered. The filtrate is evaporated to give 7-chloro-3,4,5,6-tetrahydro-β,4-methylthieno[4,3,2-ef][3]benzazepine-2-ethanamine.

EXAMPLE 37

N-[2-tetrahydro-4-methylthieno[4,3,2-ef][3]benzazepin-2-yl)propyl]benzenesulfonamide To a solution of 7-chloro-3,4,5,6-tetrahydro-β,4-methylthieno[4,3,2-ef][3]benzazepine-2-ethanamine (1.5 mmol), prepared as in Example 37, and triethylamine (2.5 ml) in tetrahydrofuran (25 ml) at 5° C. is added slowly a solution of 2-phenethyl sulfonyl chloride (1.6 mmol) in tetrahydrofuran (2.5 ml). The resulting mixture is stirred for 2 hours at room temperature, poured into a cold solution of sodium bicarbonate (8 ml), and extracted with methylene chloride. The combined extracts are washed with water, saturated sodium chloride solution, and dried over magnesium sulfate. The residue obtained after chloro-3,4,5,6-tetrahydro-4-methyl-thieno[4,3,2-ef][3]benzazepin-2-yl)propyl]benzenesulfonamide.

EXAMPLE 38

7-Chloro-3,4,5,6-tetrahydro-N,N,4-trimethyl-thieno[4,3,2-ef][3]benzazepine-2-methanamine To a solution of 7-chloro-3,4,5,6-tetrahydro-N,N,4-trimethylthieno[4,3,2-ef][3]benzazepine-2-carboxamide (9.4 mmol), prepared as in Example 19, in tetrahydrofuran (20 ml) is added diborane (10 mmol). The mixture is refluxed for 3 hours, then treated with methanol (10 ml) and dilute hydrochloric acid (10 ml). The mixture is refluxed for 30 minutes and allowed to stir at room temperature overnight. A solid is filtered from the reaction mixture to give 7-chloro-3,4,5,6-tetrahydro-N,N,4-trimethylthieno[4,3,2-ef][3]benzazepine-2-methanamine hydrochloride.

EXAMPLE 39

An oral dosage form for administering the presently invented compounds is produced by screening, mixing, and filling into a hard gelatin capsule ingredients in the proportions shown in Table II, below.

TABLE II

| Ingredients | Amounts |
| --- | --- |
| 2-[(N-Methyl-2-methylpropylsulfon-amido)methyl]-7-chloro-3,4,5,6-tetrahydro-4-methylthieno[4,3,2-ef]-[3]benzazepine | 50 mg |
| magnesium stearate | 5 mg |
| lactose | 75 mg |

EXAMPLE 40

The sucrose, calcium sulfate dihydrate and Formula (I) compound shown in Table III below, are mixed and granulated with a 10% gelatin solution. The wet granules are screened, dried, mixed with the starch, talc and stearic acid, screened and compressed into a tablet.

TABLE III

| Ingredients | Amounts |
| --- | --- |
| 7-Chloro-3,4,5,6-tetrahydro-4-methylthieno[4,3,2-ef][3]benzazepine-2-methanamine | 100 mg |
| calcium sulfate dihydrate | 150 mg |
| sucrose | 20 mg |
| starch | 10 mg |
| talc | 5 mg |
| stearic acid | 3 mg |

EXAMPLE 41

N-[(7-Chloro-3,4,5,6-tetrahydro-4-methyl-thieno[4,3,2-ef][3]benzazepin-2-yl)methyl]-2-phenyle-thenesulfonamide, 75 mg, is dispersed in 25 ml of normal saline to prepare an injectable preparation.

While the preferred embodiments of the invention are illustrated by the above, the invention is not limited to the precise instructions herein disclosed and that the right to all modifications coming within the scope of the following claims is reserved.

What is claimed is:
1. A compound of the formula:

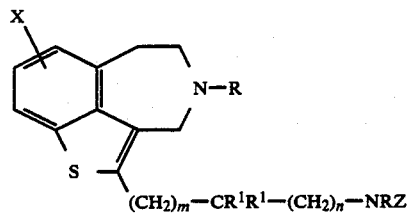

$(CH_2)_m-CR^1R^1-(CH_2)_n-NRZ$ in which:
X is H, F, Cl, Br, I, $CF_3$, $C_{1-6}$alkyl, $COR^2$, $CO_2R^2$, $CONR^3R^3$, CN, $NO_2$, $NR^4R^1$, $OR^4$, $SC_{1-4}$alkyl, $S(CH_2)_{0-6}Ph$, $SCF_3$, or any accessible synthetically stable combination thereof of up to three substituents;
each R independently is H, $C_{1-6}$alkyl, or $C_{3-5}$alkenyl, except where the double bond is in the 1-position;

each $R^1$ independently is H or $C_{1-6}$alkyl;
Z is R, $COR^5$, $CONR^3R^6$, $CO_2R^6$, $CO_2R^8$, or $SO_2R^7$;
m and n are each 0 to 2, but m+n is not greater than 2;
each $R^2$ independently is $C_{1-6}$alkyl or $(CH_2)_{0-6}Ph$;
each $R^3$ independently is H, $C_{1-6}$alkyl, or $(CH_2)_{0-6}Ph$;
each $R^4$ independently is H, $C_{1-6}$alkyl, $COR^2$, or $SO_2R^2$;
$R^5$ is H, $C_{1-6}$alkyl, $(CH_2)_{0-6}Ph$, $CH=CHPh$, $C_{3-5}$alkenyl, $(CH_2)_{1-3}OPh$, $(CH_2)_{1-3}SPh$, or $(CH_2)_{1-3}OR^1$;
$R^6$ is H, $C_{1-6}$alkyl, $(CH_2)_{0-6}Ph$, $(CH_2)_{2-3}OPh$, $(CH_2)_{2-3}SPh$, or $(CH_2)_{2-3}OR^1$;
$R^7$ is $C_{1-6}$alkyl, $(CH_2)_{0-6}Ph$, $CH=CHPh$, $C_{3-5}$alkenyl, $(CH_2)_{1-3}OPh$, $(CH_2)_{1-3}SPh$, or $(CH_2)_{1-3}OR^1$; and
$R^8$ is $C_{1-6}$alkyl, $(CH_2)_{0-6}Ph$, $(CH_2)_{2-3}Ph$, $(CH_2)_{2-3}SPh$, or $(CH_2)_{2-3}OR^1$; or a pharmaceutically acceptable salt thereof.

2. A compound of claim 1 having the formula:

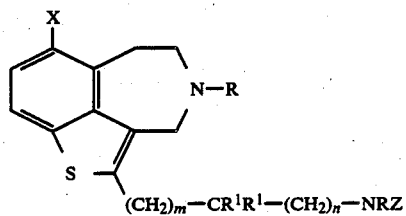

$(CH_2)_m-CR^1R^1-(CH_2)_n-NRZ$ in which
X is H, F, Cl, Br, I, $CF_3$, $C_{1-6}$alkyl, $COR^2$, $CO_2R^2$, $CONR^3R^3$, CN, $NO_2$, $NR^4R^1$, $OR^4$, $SC_{1-4}$alkyl, $(CH_2)_{0-6}Ph$, $SCF_3$, or any accessible synthetically stable combination thereof of up to three substituents;
each R independently if H, $C_{1-6}$alkyl, or $C_{3-5}$alkenyl, except where the double bond is in the 1-position;
each $R^1$ independently is H or $C_{1-6}$alkyl;
Z is R, $COR^5$, $CONR^3R^6$, $CO_2R^8$, or $SO_2R^7$;
m and n are each 0 or 2, but m+n is not greater than 2;
each $R^2$ independently is $C_{1-6}$alkyl or $(CH_2)_{0-6}Ph$;
each $R^3$ independently is H, $C_{1-6}$alkyl, or $(CH_2)_{0-6}Ph$;
each $R^4$ independently is H, $C_{1-6}$alkyl, $COR^2$, or $SO_2R^2$;
$R^5$ is H, $C_{1-6}$alkyl, $(CH_2)_{0-6}Ph$, $CH=CHPh$, $C_{3-5}$alkenyl, $(CH_2)_{1-3}OPh$ $(CH_2)_{1-3}SPh$ or $(CH_2)_{1-3}OR^1$;
$R^6$ is H, $C_{1-6}$alkyl, $(CH_2)_{0-6}Ph$ $(CH_2)_{2-3}OPh$, $(CH_2)_{2-3}SPh$, or $(CH_2)_{2-3}OR^1$;
$R^7$ is $C_{1-6}$alkyl, $(CH_2)_{0-6}Ph$, $CH=CHPH$, $C_{3-5}$alkenyl, $(CH_2)_{1-3}OPh$, $(CH_2)_{1-3}SPH$, or $(CH_2)_{1-3}OR^1$; and
$R^8$ is $C_{1-6}$alkyl, $(CH_2)_{0-6}Ph$, $(CH_2)_{2-3}OPh$, $(CH_2)_{2-3}SPh$, or $(CH_3)_{2-3}OR^1$; or a pharmaceutically acceptable salt thereof.

3. A compound of claim 2 wherein X is F, Cl, Br, or I.

4. A compound of claim 3 wherein R is $CH_3$.

5. A compound of claim 4 that is N-[(7-chloro-3,4,5,6-tetrahydro-4-methylthieno[4,3,2-ef][3]benzazepin-2-yl)methyl]-2-methylpropanesulfonamide.

6. A compound of claim 4 that is:
7-chloro-3,4,5,6-tetrahydro-4-methylthieno[4,3,2-ef][3]benzazepine-2-methanamine;
N-[(7-chloro-3,4,5,6-tetrahydro-4-methylthieno[4,3,2-ef][3]benzazepin-2-yl)methyl]-2-phenylethenesulfonamide;

N-[(7-chloro-3,4,5,6-tetrahydro-4-methylthieno[4,3,2-ef][3]benzazepin-2-yl)methyl]-2-benzeneethanesulfonamide; or N-[(7-chloro-3,4,5,6-tetrahydro-4-methylthieno[4,3,2-ef][3]benzazepin-2-methyl]-2-benzenesulfonamide.

7. A pharmaceutical composition comprising an effective amount of a compound of claim 1 and a suitable pharmaceutical carrier.

8. A pharmaceutical composition of claim 7 wherein the compound is N-[(7-chloro-3,4,5,6-tetrahydro-4-methylthieno[4,3,2-ef][3]benzazepin-2-yl)methyl]-2-methylpropanesulfonamide.

9. A pharmaceutical composition of claim 7 wherein the compound is:

7-chloro-3,4,5,6-tetrahydro-4-methylthieno[4,3,2-ef][3]benzazepine-2-methanamine;

N-[(7-chloro-3,4,5,6-tetrahydro-4-methylthieno[4,3,2-ef][3]benzazepin-2-yl)methyl]-2-phenylethenesulfonamide;

N-[(7-chloro-3,4,5,6-tetrahydro-4-methylthieno[4,3,2-ef][3]benzazepin-2-yl)methyl]-2-benzeneethanesulfonamide; or N-[(7-chloro-3,4,5,6-tetrahydro-4-methylthieno[4,3,2-ef][3]benzazepin-2-methyl]-2-benzenesulfonamide.

10. A method of antagonizing α-adrenergic receptors in mammals that comprises administering to a subject in need thereof an effective amount of a compound of claim 1.

11. A method of claim 10 wherein the compound is N-[(7-chloro-3,4,5,6-tetrahydro-4-methylthieno[4,3,2-ef][3]benzazepin-2-yl)methyl-2-methylpropanesulfonamide.

12. A method of claim 10 wherein the compound is:

7-chloro-3,4,5,6-tetrahydro-4-methylthieno[4,3,2-ef][3]benzazepine-2-methanamine;

N-[(7-chloro-3,4,5,6-tetrahydro-4-methylthieno[4,3,2-ef][3]benzazepin-2-yl)methyl]-2-phenylethenesulfonamide;

N-[(7-chloro-3,4,5,6-tetrahydro-4-methylthieno[4,3,2-ef][3]benzazepin-2-yl)methyl]-2-benzeneethanesulfonamide; or N-[(7-chloro-3,4,5,6-tetrahydro-4-methylthieno[4,3,2-ef][3]benzazepin-2-methyl]-2-benzenesulfonamide.

13. A method of reducing blood pressure in mammals that comprises administering to a subject in need thereof an effective amount of a compound of claim 1.

14. A method of treating cardiovascular diseases in mammals that comprises administering to a subject in need thereof an effective amount of a compound of claim 1.

15. A method of treating benign prostatic hypertrophy in mammals that comprises administering to a subject in need thereof an effective amount of a compound of claim 1.

16. A method of treating depression in mammals that comprises administering to a subject in need thereof an effective amount of a compound of claim 1.

17. A method of treating obesity in mammals that comprises administering to a subject in need thereof an effective amount of a compound of claim 1.

18. A method of treating diabetis in mammals that comprises administering to a subject in need thereof an effective amount of a compound of claim 1.

* * * * *

UNITED STATES PATENT AND TRADEMARK OFFICE
CERTIFICATE OF CORRECTION

PATENT NO. : 4,981,848

DATED : January 1, 1991

INVENTOR(S) : Thomas W. Ku

It is certified that error appears in the above-identified patent and that said Letters Patent is hereby corrected as shown below:

In Claim 1, column 26, line 2, after "$CON^{R_3}R^6$" delete "$CO_2R^6$".

In Claim 1, column 26, line 15, replace "$(CH_2)_{2-3}PH$" with --- $(CH_2)_{2-3}OPH$ ---.

Signed and Sealed this

Twenty-sixth Day of May, 1992

*Attest:*

DOUGLAS B. COMER

*Attesting Officer*  *Acting Commissioner of Patents and Trademarks*